United States Patent [19]

Coles

[11] 4,232,660
[45] Nov. 11, 1980

[54] WINGED IRRIGATING SURGICAL RETRACTOR

[76] Inventor: Robert L. Coles, 13 New Haven Dr., Greenville, S.C. 29615

[21] Appl. No.: 24,047

[22] Filed: Mar. 26, 1979

Related U.S. Application Data

[63] Continuation of Ser. No. 779,362, Mar. 21, 1977, abandoned.

[51] Int. Cl.³ .............................................. A61B 17/02
[52] U.S. Cl. .................................. 128/20; 128/303 R
[58] Field of Search ................. 128/3, 12, 15, 20, 17, 128/18, 19, 224, 239, 240, 303 R

[56] References Cited

U.S. PATENT DOCUMENTS

| | | | |
|---|---|---|---|
| 374,122 | 11/1887 | Genese | 128/15 |
| 412,409 | 10/1889 | Osborne | 128/15 |
| 465,161 | 12/1891 | Chase | 128/15 |
| 990,277 | 8/1910 | Lauderdale | 128/15 |
| 1,498,267 | 6/1924 | Hachman | 128/15 |
| 2,854,004 | 9/1958 | Durrant | 128/15 |
| 2,947,305 | 8/1960 | Storz | 128/12 |
| 3,332,414 | 7/1967 | Gasper | 128/17 |
| 3,626,471 | 12/1971 | Florin | 128/20 |
| 3,651,800 | 3/1972 | Wilbanks | 128/12 |
| 3,731,673 | 5/1973 | Halloran | 128/20 |
| 3,796,214 | 3/1974 | Davis | 128/20 |
| 4,049,000 | 9/1977 | Williams | 128/20 |

FOREIGN PATENT DOCUMENTS 129789  3/1959  U.S.S.R. ............................ 128/303 R

OTHER PUBLICATIONS

The Thompson Ramus Retractor; in Walter Lorenz Surgical Instruments Catalog-144 W. 27th Str., NY, NY; pp. 9,11,21.
*Mueller Catalog;* Oral Instruments-p. 120, 1938.

*Primary Examiner*—Robert W. Michell
*Assistant Examiner*—Arthur S. Rose
*Attorney, Agent, or Firm*—Bailey, Dority & Flint

[57] ABSTRACT

A surgical device for surgical procedures requiring exposure and visibility of the facial skeletal areas comprises an elongated blade member having a handle portion adjacent one end and a curved lip portion adjacent the distal end for forming a fulcrum with an associated bone process and a pair of wing projections laterally inclined from the blade member providing increased retraction of soft tissue and muscle in the surgical working area. An integral irrigating conduit is provided for delivering a flush of water to the surgical working area as required for cleaning.

5 Claims, 4 Drawing Figures

WINGED IRRIGATING SURGICAL RETRACTOR

This is a continuation of application Ser. No. 779,362, filed Mar. 21, 1977, now abandoned.

BACKGROUND OF THE INVENTION

In surgical procedures requiring exposure and visibility of areas of the facial skeleton such as the jaw area, it is necessary that the soft tissue and muscle in the working area be retracted to avoid any possible damage or severance thereof. Access may then be had in the working area without obstruction. Visibility and stability in the operational procedure is enhanced when a stable point such as a bone process is utilized as a fulcrum for retraction.

Prior retraction devices have been developed such as the retractor commonly known as the Thompson Ramus Retractor which has been valuable in arthroplasties, condylar fractures, and prognathic and retrognathic corrections. This device includes a single blade of metal bent upon itself to form a handle portion and a retractor portion having a curved lip at the end thereof for fitting over a bone process to provide a fulcrum for retraction as best illustrated in the enclosed pages from the catalogue of Walter Lorenz Surgical Instruments, 144 West 27th Street, New York, N.Y. The blade of the retractor is used as a straight edge for making incisions and for retracting the tissue and muscle in the working area. However, the retracting surface is limited to the width of the blade which limits the amount of tissue and muscle retracted and hence the area of exposure.

SUMMARY OF THE INVENTION

A retractor device for use in surgical procedures involving the facial skeleton, particularly the jaw and oral areas, is disclosed comprising an elongated blade member having a handle portion adjacent on end thereof and a curved lip formed adjacent a distal end of said elongated blade member adapted for fitting over a bone process to form a fulcrum therewith. A pair of opposed wing projections extend laterally in an inclined manner from the blade member providing an enlarged retracting surface and forming an arcuate bridge over the surgical working area for retracting and supporting tissue and muscle to provide increased access to the surgical working area.

Accordingly, an important object of the present invention is to provide a surgical device for retracting muscle and tissue which provides increased exposure and visibility of the surgical working area.

Still another important object of the present invention is the provision of a surgical retracting device having laterally extending projections providing a bridge over a surgical working area and providing an enlarged retracting surface.

Yet another important object of the present invention is to provide a surgical device for retraction of skin and muscle tissues which provides irrigation of the working area without utilizing additional instruments which compete for space in the working area.

BRIEF DESCRIPTION OF THE DRAWING

The construction designed to carry out the invention will be hereinafter described, together with other features thereof.

The invention will be more readily understood from a reading of the following specification and by reference to the accompanying drawing forming a part thereof, wherein an example of the invention is shown and wherein.

DESCRIPTION OF A PREFERRED EMBODIMENT

Figure 1:
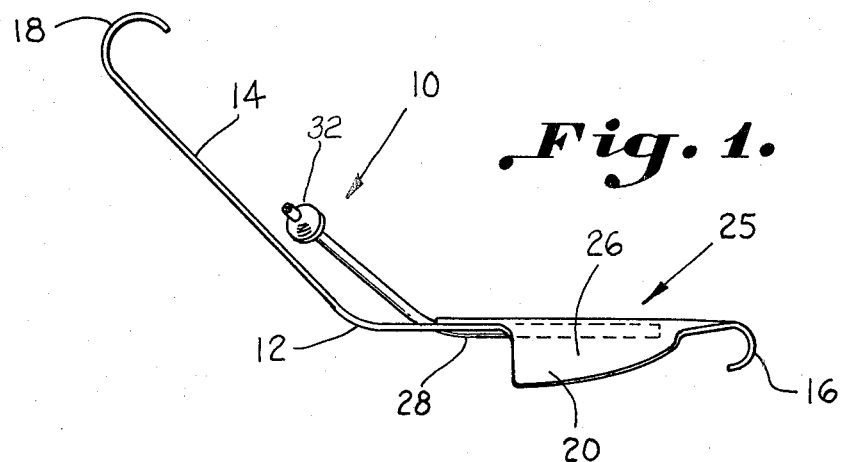
FIG. 1 is a side elevational view illustrating a winged irrigating retractor device constructed in accordance with the present invention.
Figure 2:
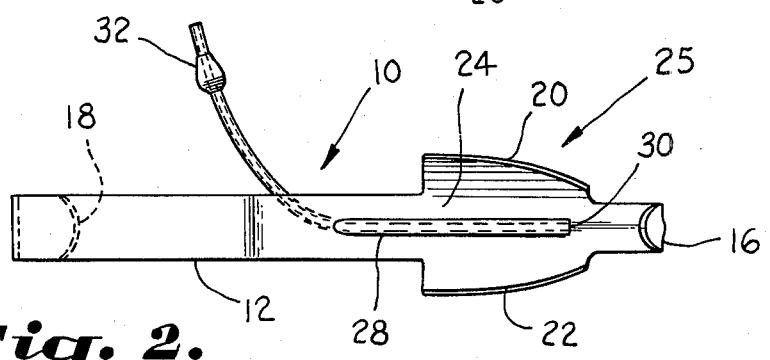
FIG. 2 is a bottom plan view of the device of FIG. 1.

The invention relates to an irrigating retractor device for use in surgical procedures involving the facial skeleton and more particularly the jaw and oral areas wherein it is desirable for cosmetic purposes to make a small incision and insert the surgical device into the incision and retract the soft tissue and muscles to provide exposure and visibility for operating on a bone structure.

Referring now in more detail to the drawing, a surgical device designated generally at 10 is illustrated as including an elongated blade member 12 having a distal and a proximal end, and a handle portion 14 connected to the proximal end thereof and a curved lip portion 16 formed adjacent a distal end thereof. The curved lip 16 is adapted for fitting over a bone process to form a fulcrum about which the instrument may be pivoted for retracting the soft tissue and muscle from the surgical area. The handle portion 14 terminates in a curved lip 18 which enables the surgical device to be held in a more stable manner.

A pair of opposed wing projections 20 and 22 extend laterally from the blade member 12 in an area adjacent the curved lip 16 for providing an enlarged retracting surface. The laterally extending projections 20 and 22 are inclined downwardly and together with a medial portion 24 of a length of the blade member 12, which extends contiguously between the wing projections in the middle thereof, define a bridge, designated generally as 25, over the surgical working area which supports the soft tissue and muscle in a retracted position while providing access to the surgical working area beneath the bridge. As illustrated, the laterally extending projections 20 and 22 are slightly curved to define an arcuate-shaped bridge presenting a rounded upper surface 26 so that insertion through an incision and underneath the tissue and muscle may be made smoothly without interference from sharp surfaces or edges.

Means for irrigating the surgical working area is provided by a conduit 28 integrally carried flush with the bottom of the elongated blade member 12 so as to extend longitudinally along the blade between the lateral wing members 20 and 22. The conduit has an outlet opening 30 for delivering a flush of water to the working area for irrigating and cleaning the area. It is to be understood, of course, that other openings may be provided in the bottom of tubing 28 so as to provide spaced streams of the irrigating or flushing water to the working area. The remote end of conduit 28 includes a coupling member 32 which is adapted for connection to a conventional syringe 34 by means of a length of flexible tubing 36. The syringe member 34 may be filled with a supply of sterile water for irrigating the working area through the conduit means 28. The device so constructed provides the expedient of eliminating a separate irrigating instrument which would otherwise compete for space within the working area during surgical procedures.

Figure 3:
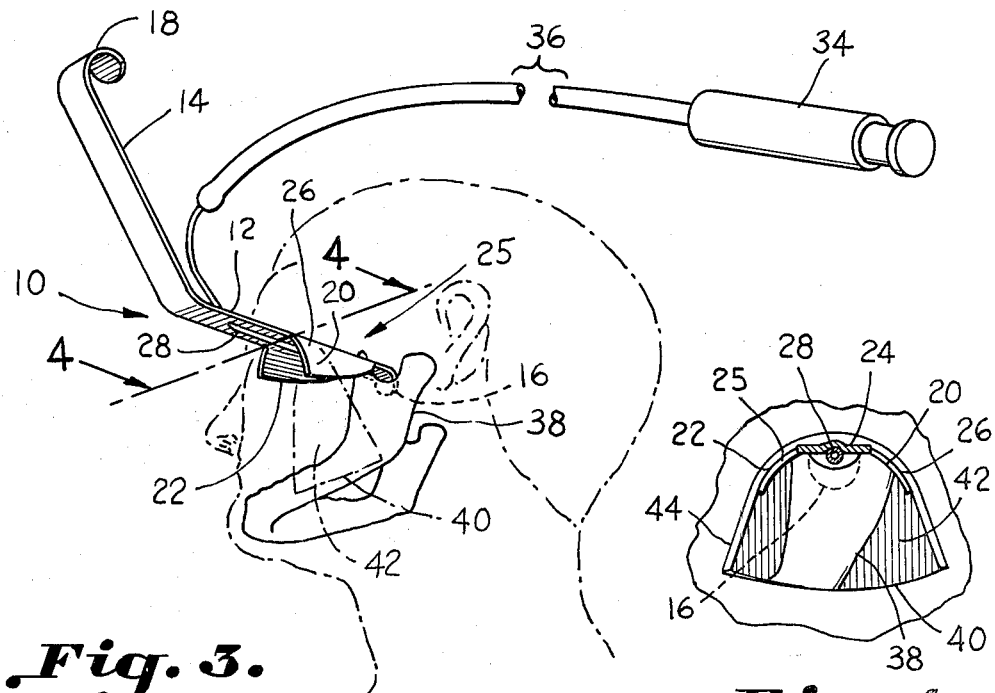
FIG. 3 is a perspective view illustrating a surgical procedure utilizing the winged irrigating retractor device constructed in accordance with the present invention.
Figure 4:
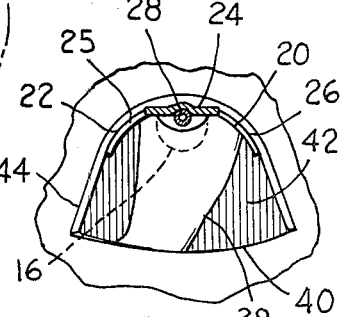
FIG. 4 is an enlarged view of an area taken along line 4—4 of FIG. 3 illustrating the exposure and visibility of the lower jaw bone as provided by retraction of the tissues and masseter muscle with the device of the present invention.

Referring now to FIGS. 3 and 4, the surgical retractor device 10 is illustrated in a surgical procedure involving the ramus area where the curved lip 16 may be advantageously fitted over the sigmoid notch of the ramus 38. In this position the retractor is suitable for surgical procedures such as repairing joints of the jaw or making artificial joints and/or making any other corrections to the facial bone and jaw structure in this area. With the device 10 inserted through a small incision 40 slightly below the lower jaw portion, the curved lip 16 is fitted over the sigmoid notch. The device is then lifted and the tissue and muscle bundles retracted to provide an access opening and space 42 as best seen in FIG. 4 through which access may be had for carrying out the surgical process.

As illustrated in FIG. 4, the lateral wing projections 20 and 22 support the layer 44 of skin and muscle tissue in a retracted position from the incision upward to define an access opening in the form of an arch. A tunnel space having an enlarged width extends beneath the bridge and archway structure from the opening to the notch area providing unobstructed access to the surgical working area reducing accidental muscle and tissue damage.

The masseter muscle bundle which extends from the zigomatic arch to the lower portion of the jaw will be retracted sufficiently above the surgical working area to reduce any possibility of severence thereof.

Thus, it can be seen that an advantageous construction of a surgical instrument can be had in accordance with the present invention wherein an enlarged retracting surface is provided increasing exposure and visibility of the surgical working area. The instrument cleans the working area by irrigation and eliminates the need for a separate instrument which would otherwise compete for space in the working area further enhancing unobstructed access thereto. Thus, the instrument of the present invention provides two functions in the surgical procedure in a manner producing a greater overall advantage than the two functions taken separately.

While a preferred embodiment of the invention has been described using specific terms, such description is for illustrative purposes only, and it is to be understood that changes and variations may be made without departing from the spirit or scope of the following claims.

What is claimed is:

1. A retractor device for use in surgical procedures in a surgical working area involving the jaw and oral areas comprising:

an elongated generally straight blade member having a distal end and a proximal end;

a curved element connected to said distal end of said blade member, said curved element being inclined downwardly from said blade member and being adapted for fitting over a bone process to form a fulcrum therewith;

a pair of opposed wing projections extending laterally in an inclined manner from said blade member providing an enlarged retracting surface for retracting tissue and muscle to provide access to said surgical working area and avoiding damage of adjacent tissue and muscle;

an elongated, generally flat, generally straight handle portion having a first and a second end, said first end of said handle portion being connected to said proximal end of said blade member;

said elongated blade member including a generally flat portion extending from said proximal end of said blade member to said distal end of said blade member and intermediately connecting said flat portion of said handle portion and said wing projections for providing an unrestricted side view of and access to said surgical working area;

said handle portion being substantially inclined and extending away from said flat portion of said elongated blade member in a direction opposite to the inclination of said curved element; and conduit means carried by said elongated blade member having at least one outlet for delivering a flush of water to said working area, said outlet of said conduit means being disposed at a spaced distance from said curved element and said distal end of said elongated blade and generally above said surgical working area when inserted therein so as to cause downward delivery of said water to said surgical working area in a flushing stream pattern and facilitate unrestricted viewing and working in said working area, and a remote end of said conduit means being adapted for connection to a syringe member for delivering said flush of water.

2. The device as set forth in claim 1 wherein said wing projections are inclined downwardly and cooperate with a portion of the length of said blade member for defining a bridge over said working area retracting and supporting the tissue and muscle therefrom while providing access thereunder for surgical procedures in said working area.

3. The device as set forth in claim 2 wherein said wing projections are curved to define an arcuate shaped bridge having a rounded uninterrupted upper surface for smooth insertion under the skin and muscle tissue.

4. The device as set forth in claim 1 wherein said wing projections are curved to define an arcuate shaped bridge having a rounded uninterrupted upper surface for smooth insertion under the skin and muscle tissue.

5. The device as set forth in claim 1 wherein said wing projections taper inwardly toward said distal end for smooth insertion within an incision and increased rearward access.

* * * * *